(12) United States Patent
Barral

(10) Patent No.: US 11,501,871 B2
(45) Date of Patent: *Nov. 15, 2022

(54) ENHANCED PATHOLOGY DIAGNOSIS

(71) Applicant: Verily Life Sciences LLC, South San Francisco, CA (US)

(72) Inventor: Joëlle K. Barral, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 16/288,456

(22) Filed: Feb. 28, 2019

(65) Prior Publication Data

US 2019/0198160 A1 Jun. 27, 2019

Related U.S. Application Data

(63) Continuation of application No. 16/008,809, filed on Jun. 14, 2018, now Pat. No. 10,262,757, which is a
(Continued)

(51) Int. Cl.
*G16H 30/40* (2018.01)
*G06N 20/00* (2019.01)
(Continued)

(52) U.S. Cl.
CPC ........... *G16H 30/40* (2018.01); *A61B 5/7264* (2013.01); *G06F 16/58* (2019.01); *G06K 9/6255* (2013.01);
(Continued)

(58) Field of Classification Search
CPC ........ G16H 30/40; G16H 10/40; G16H 30/20; G16H 50/20; G06F 16/58; G06F 19/00;
(Continued)

(56) References Cited

U.S. PATENT DOCUMENTS 6,005,964 A 12/1999 Reid et al.
6,441,958 B1 8/2002 Yeung et al.
(Continued)

FOREIGN PATENT DOCUMENTS

JP H052050 A 8/1993
JP 2003093380 A 4/2003
(Continued)

OTHER PUBLICATIONS

NPL Search History (Year: 2021).*
(Continued)

*Primary Examiner* — Nancy Bitar
(74) *Attorney, Agent, or Firm* — Christensen O'Connor Johnson Kindness PLLC

(57) ABSTRACT

A system includes a microscope configured to magnify a pathology sample, a camera positioned to record magnified pathology images from the microscope, and a display configured to show the magnified pathology images. A processing apparatus is coupled to the camera, and the display, and the processing apparatus includes instructions that when executed by the processing apparatus cause the system to perform operations, including: identifying, using a machine learning algorithm, one or more regions of interest in the magnified pathology images; and alerting, using the display, a user of the microscope to the one or more regions of interest in the magnified pathology images while the pathology sample is being magnified with the microscope.

20 Claims, 4 Drawing Sheets

Related U.S. Application Data continuation of application No. 15/235,541, filed on Aug. 12, 2016, now Pat. No. 10,025,902.

(51) Int. Cl.
| | |
|---|---|
| *G06F 16/58* | (2019.01) |
| *G16H 10/40* | (2018.01) |
| *G06K 9/62* | (2022.01) |
| *G16Z 99/00* | (2019.01) |
| *G06V 10/25* | (2022.01) |
| *G06V 20/69* | (2022.01) |
| *G06V 40/18* | (2022.01) |
| *G16H 50/20* | (2018.01) |
| *G06T 7/00* | (2017.01) |
| *A61B 5/00* | (2006.01) |
| *G16H 30/20* | (2018.01) |

(52) U.S. Cl.
CPC ........... *G06N 20/00* (2019.01); *G06T 7/0014* (2013.01); *G06V 10/25* (2022.01); *G06V 20/698* (2022.01); *G06V 40/18* (2022.01); *G16H 10/40* (2018.01); *G16H 30/20* (2018.01); *G16H 50/20* (2018.01); *G16Z 99/00* (2019.02); *G06T 2207/10056* (2013.01); *G06T 2207/20081* (2013.01); *G06T 2207/30024* (2013.01); *G06V 2201/10* (2022.01)

(58) Field of Classification Search
CPC .. G06F 19/345; G06N 20/00; G06K 9/00147; G06K 9/00597; G06K 9/3233; G06K 9/6255; G06K 2209/27; G06T 7/0014; G06T 2207/10056; G06T 2207/20081; G06T 2207/30024; A61B 5/7264
See application file for complete search history.

(56) References Cited

U.S. PATENT DOCUMENTS

| | | | |
|---|---|---|---|
| 8,199,358 B2 | 6/2012 | Eichhorn et al. | |
| 8,350,905 B2 | 1/2013 | Yamada | |
| 8,600,143 B1 | 12/2013 | Kulkarni et al. | |
| 9,373,168 B2 | 6/2016 | Van Leeuwen et al. | |
| 9,710,695 B2 * | 7/2017 | Xu | G06K 9/6273 |
| 10,262,757 B2 * | 4/2019 | Barral | A61B 5/7264 |
| 2002/0135678 A1 * | 9/2002 | Bacus | G02B 21/0004 |
| | | | 348/143 |
| 2004/0081343 A1 | 4/2004 | Takeo et al. | |
| 2004/0120557 A1 | 6/2004 | Sabol et al. | |
| 2004/0122705 A1 | 6/2004 | Sabol et al. | |
| 2005/0010445 A1 | 1/2005 | Krishnan et al. | |
| 2006/0159367 A1 | 7/2006 | Zeineh et al. | |
| 2008/0082468 A1 * | 4/2008 | Long | G06K 9/6269 |
| | | | 706/12 |
| 2011/0206283 A1 * | 8/2011 | Quarfordt | G06V 40/193 |
| | | | 382/220 |
| 2012/0004514 A1 | 1/2012 | Marugame | |
| 2012/0188283 A1 * | 7/2012 | Ohashi | G06K 9/6254 |
| | | | 382/128 |
| 2013/0342674 A1 | 12/2013 | Dixon | |
| 2015/0072371 A1 * | 3/2015 | Marugame | G16Z 99/00 |
| | | | 702/19 |
| 2015/0130920 A1 | 5/2015 | Zou et al. | |
| 2016/0110584 A1 * | 4/2016 | Remiszewski | G06V 20/69 |
| | | | 382/133 |

FOREIGN PATENT DOCUMENTS

| | | |
|---|---|---|
| JP | 2005182670 A | 7/2005 |
| JP | 2007528746 A | 10/2007 |
| JP | 2010035756 A | 2/2010 |
| JP | 2012143369 A | 8/2012 |
| JP | 2012523877 A | 10/2012 |
| JP | 2016085715 A | 5/2016 |
| WO | 2005/121863 A1 | 12/2005 |

OTHER PUBLICATIONS

Japanese Office Action, with English Translation, dated Mar. 23, 2020, for corresponding Japanese Patent Application No. 2019-505009, 11 pages.
Gurcan M.N. et al., "Histopathological Image Analysis: A Review," IEEE Reviews in Biomedical Engineering, vol. 2, 2009, 26 pages.
Nodine C.F. et al., "Using eye movements to study visual search and to improve tumor detection," RadioGraphics, vol. 7, No. 6, Monograph, Nov. 1987, 10 pages.
International Search Report and Written Opinion from the International Searching Authority dated Oct. 26, 2017, for International Application No. PCT/US2017/046125, filed Aug. 9, 2017, 14 pages.
European Office Action, dated May 6, 2021, in corresponding European Patent Application No. 17757613.9, 6 pages.
Japanese Office Action, dated Feb. 4, 2022, in corresponding Japanese Patent Application No. 2020213040, 5 pages.

* cited by examiner

ENHANCED PATHOLOGY DIAGNOSIS

REFERENCE TO RELATED APPLICATION

This application is a continuation of U.S. application Ser. No. 16/008,809, filed Jun. 14, 2018, which is a continuation of U.S. application Ser. No. 15/235,541, filed on Aug. 12, 2016, now U.S. Pat. No. 10,025,902, the contents of which are incorporated herein by reference.

TECHNICAL FIELD

This disclosure relates generally to systems/methods for aiding in pathology.

BACKGROUND INFORMATION

Pathology is a medical discipline related to the study and diagnosis of disease. Most frequently pathology involves the analysis and examination of body-fluid, tissue, and cell samples. As a field of general study and research, pathology relates to four aspects of disease: (1) etiology, (2) pathogenesis, (3) morphologic changes, and (4) consequence of morphologic changes.

The field of pathology dates back to Antiquity. Many early societies possessed a rudimentary understanding of biological conditions as a result of dissection/examination. By the Hellenic period of Greece, a causal study of disease had emerged in human culture. Human understanding of disease through pathology continued to advance piecemeal as time progressed; for instance many advances in pathology are attributable to the medieval era of Islam.

However, modern pathology only emerged as a distinct field of study in the late 1800's with the advent of microbiology. Now pathology is a major medical practice that is divided into a number of subdisciplines. In all of these subdisciplines, having a second opinion to check the work of a pathologist is helpful to eliminate erroneous diagnosis. Eliminating diagnostic error in pathology may result in a healthier population and reduce pathologists' exposure to liability.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for enhanced pathology diagnosis are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The instant disclosure provides a system and method for enhancing pathology diagnosis. More specifically, these systems and methods may be used to aid a pathologist in the diagnosis of disease. A machine learning algorithm may be trained to alert pathologists to regions of interest (e.g., diseased tissue, atypical cells, unusual growth, etc.) in a pathology sample when the machine learning algorithm recognizes these regions in the sample. Providing a second opinion to pathologists may both increase pathologist efficiency (by allowing the pathologist to spend less time on each slide), and decrease the probability of an inaccurate diagnosis (by alerting the pathologists to regions of interest in the sample).

Figure 1:
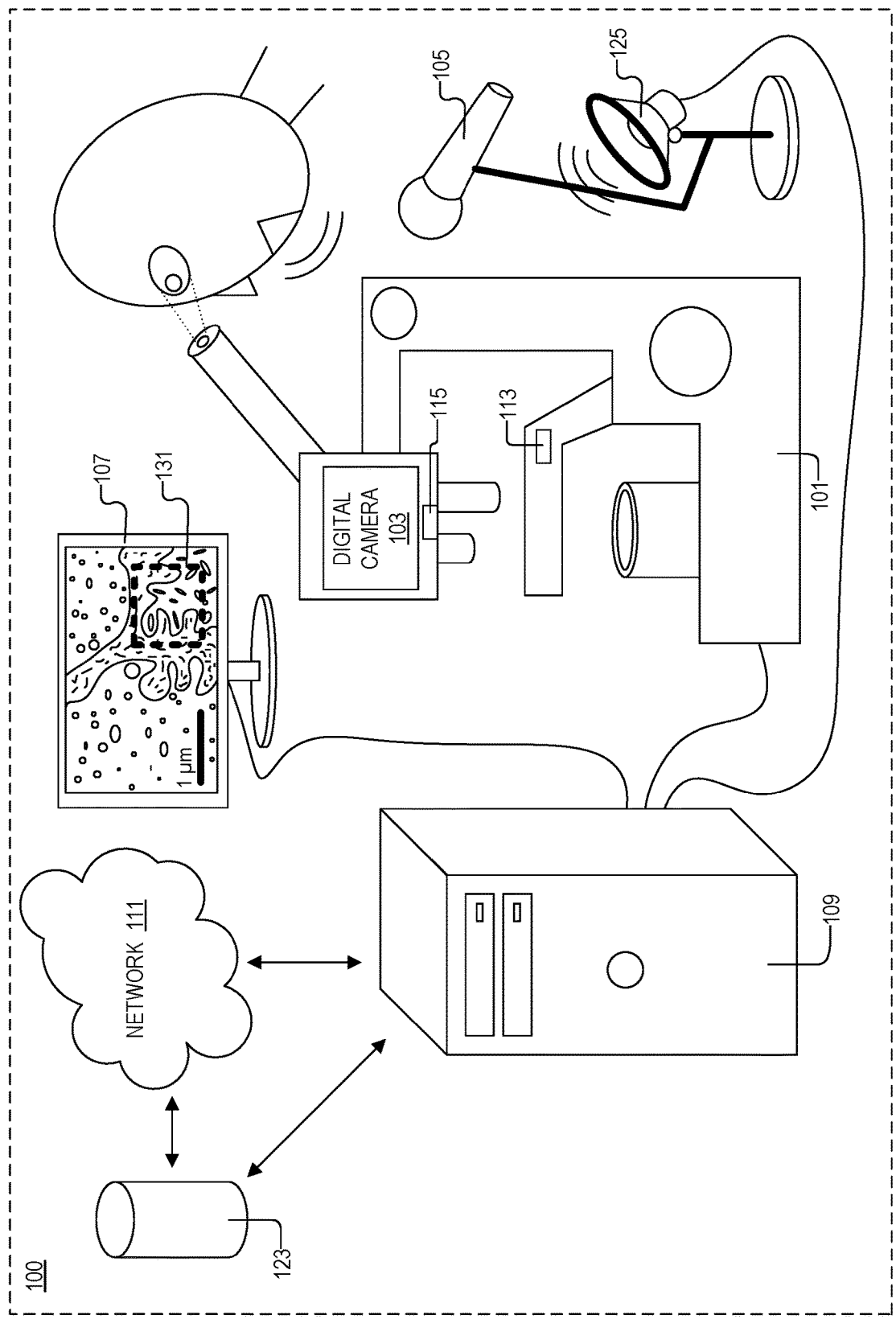
FIG. 1 illustrates a system for pathology diagnosis, in accordance with an embodiment of the disclosure.

FIG. 1 illustrates a system 100 for pathology diagnosis, in accordance with an embodiment of the disclosure. System 100 includes: microscope 101, digital camera 103, microphone 105, screen 107, processing apparatus 109, network 111, storage 123, speaker 125, first mechanical to electrical transducer 113, and second mechanical to electrical transducer 115.

In the illustrated embodiment, the user (e.g., a pathologist) is looking at a magnified pathology sample with microscope 101. Microscope 101 is magnifying a pathology sample to form magnified pathology images. The magnified pathology images are recorded with digital camera 103 optically coupled to microscope 101. Digital camera 103 is electrically coupled (wired or wirelessly) to processing apparatus 109 (e.g., a desktop computer, server, etc.) to send the magnified pathology images (still-frames or video) to processing apparatus 109. Processing apparatus 109 compares the magnified pathology images to reference pathology images included in a pathology database (contained on remote or local storage 123) to identify one or more regions of interest (e.g., outlined portion 131 on screen 107) in the magnified pathology images. If there is a region of interest in the magnified pathology images, system 100 may alert the user of microscope 101 to the one or more regions of interest. This alert may be an audio alert (e.g., voice from speaker 125 saying "look in the lower left hand corner of the image there may be cancer"), visual alert (e.g., highlighting the region of interest 131 on screen 107), or haptic alert (e.g., vibrating the stage of microscope 101) in response to identifying the one or more regions of interest.

In one embodiment, a machine learning algorithm (see infra FIG. 2) is used to identify the one or more regions of interest, and is trained to identify the one or more regions of interest using the reference pathology images in the pathology database. The pathology database may include many combinations of reference pathology images, annotations from a pathologist, and grading/diagnosis from a pathologist. On processing apparatus 109, image processing and machine learning algorithms may be running so that image data from digital camera 103 is interpreted in real time and guidance can be provided to the user (pathologist) either visually on the monitor or by audio feedback (e.g., "prostate adenocarcinoma Gleason score 6", "slide folded", "image out of focus", etc.). Headphones can be added to system 100 for convenience, and the conversation can be recorded and archived with respect to the video/images captured by digital camera 103.

Reference images in the pathology database may include hundreds of thousands, or even millions, of images of pathology samples that the machine learning algorithm has been trained to recognize as diseased or healthy tissue. Moreover, the pathology database may also include annotations from a trained pathologist corresponding to the reference pathology images in the pathology database (see infra FIG. 2). The machine learning algorithm may use the annotations from the pathologist in conjunction with the reference pathology images to train itself to identify the one or more regions of interest in the magnified pathology images. The pathology database may include transcribed text that the pathologist spoke when the reference pathology images were recorded. For example, the pathologist recording the images in the database may have said "this portion of the sample looks normal." The machine learning algorithm may receive this statement from the database as either natural language or transcribed text, and know that the portion of the sample the pathologist is referring to has nothing interesting in it. The machine learning algorithm may note the characteristics of the sample that make it "normal" and recognize these characteristics in future images. Alternatively, the pathologist may have made a statement about the sample being malignant and the machine learning algorithm may note the characteristics of the malignant sample, and apply this knowledge of malignant samples to future magnified pathology images.

In one embodiment, the pathology database further includes slide position information and magnification information about the reference pathology images in the pathology database. For example, when reference samples were included in the database either as still photos or videos, the location of where the microscope was focusing (slide position information) may have been recorded—this may include the relative coordinates on the sample, the position of the microscope stage, etc. Similarly, the level of magnification used to see the features in the reference pathology images may also be recorded. For example, it may be useful for the machine learning algorithm to know what magnification was used when a determination of either "benign" or "malignant" was made, since certain features may only be visible under certain magnifications. The machine learning algorithm may use the slide position information and magnification information to identify the one or more regions of interest in the magnified pathology images.

In the illustrated embodiment, system 100 may identify areas of the pathology sample that are deemed to be insufficiently reviewed by the user, and inform the user of one or more regions of potential interest (e.g., a region of the sample that may appear to system 100 as containing diseased, cancerous, or otherwise interesting tissue/fluid/etc.) in the areas that were deemed to be insufficiently reviewed by the user. For example, if the user of system 100 is examining a pathology sample and inadvertently passes over a region that system 100 recognizes as possibly important, system 100 may alert the user to the presence of the one or more regions of potential interest. Alerting the user may be achieved in the ways discussed above (e.g., via audio, visual, haptic, or other methods). In one embodiment, the machine learning algorithm may be trained to identify the areas of the pathology sample that are deemed to be insufficiently reviewed by the user based on the user viewing the areas for a threshold amount of time. In one example, this may involve the machine learning algorithm tracking if a sample was in the user's field of view for a threshold amount of time. For example, if the user of system 100 spends less than one second looking at an area in the pathology sample, system 100 may presume that that area of the sample was passed over.

However, system 100 may be more refined, and use more than just time as the sole metric of if a portion of the sample was insufficiently reviewed. This is because a trained pathologist may simply need to glance at one area of a pathology sample and know immediately it is not of interest. Accordingly, system 100 may determine that a user has/has not viewed specific areas by employing at least one of gaze detection (illustrated as dashed lines from the eyepiece of microscope 101 in FIG. 1), location of the pathology sample (e.g., stage position or relative position on the sample), or level of magnification of microscope 101. Thus, if the trained pathologist misses an area in the pathology sample because he/she never even looked at it, system 100 may use gaze detection (e.g., pupal dilation) and alert the pathologist that he/she passed over this portion of the sample.

In the illustrated embodiment, processing apparatus 109 is coupled (wired or wirelessly) to network 111 and/or storage 123. Network 111 and storage 123 may be local or remote, and may or may not be distributed. Storage 123 may include RAM, ROM, hard disks, flash memory, or any other suitable memory system. Network 111 may include the internet or local area network. In one embodiment, processing apparatus 109 may be a distributed system on network 111. One skilled in the art will appreciate that there are any number of ways to process/store data in accordance with the teachings of the present disclosure.

In the depicted embodiment, microphone 105 is electrically coupled to processing apparatus 109 (either wired or wirelessly) to record what the pathologist says. This information may be used to update the pathology database and further teach the machine learning algorithm. Additionally, images captured by digital camera 103 may also be used to update the pathology database along with the microscope stage position (provided by mechanical to electrical transducer 113) and level of magnification (provided by mechanical to electrical transducer 115).

In some embodiments, system 100 may be used to help pathologists transition to a fully digital microscopy environment, and a mouse is coupled to processing apparatus 109 and/or microscope 101. The mouse may control a motorized stage on microscope 101. The pathologist could choose to either physically move the slide (by turning nobs on the microscope) or the pathologist could move the mouse, and the motorized stage would move the slide to the corresponding location. In one embodiment, the motion of the stage could be captured to further inform the machine learning algorithm (e.g., to figure out which parts of the slide have been neglected/passed over).

Figure 2:
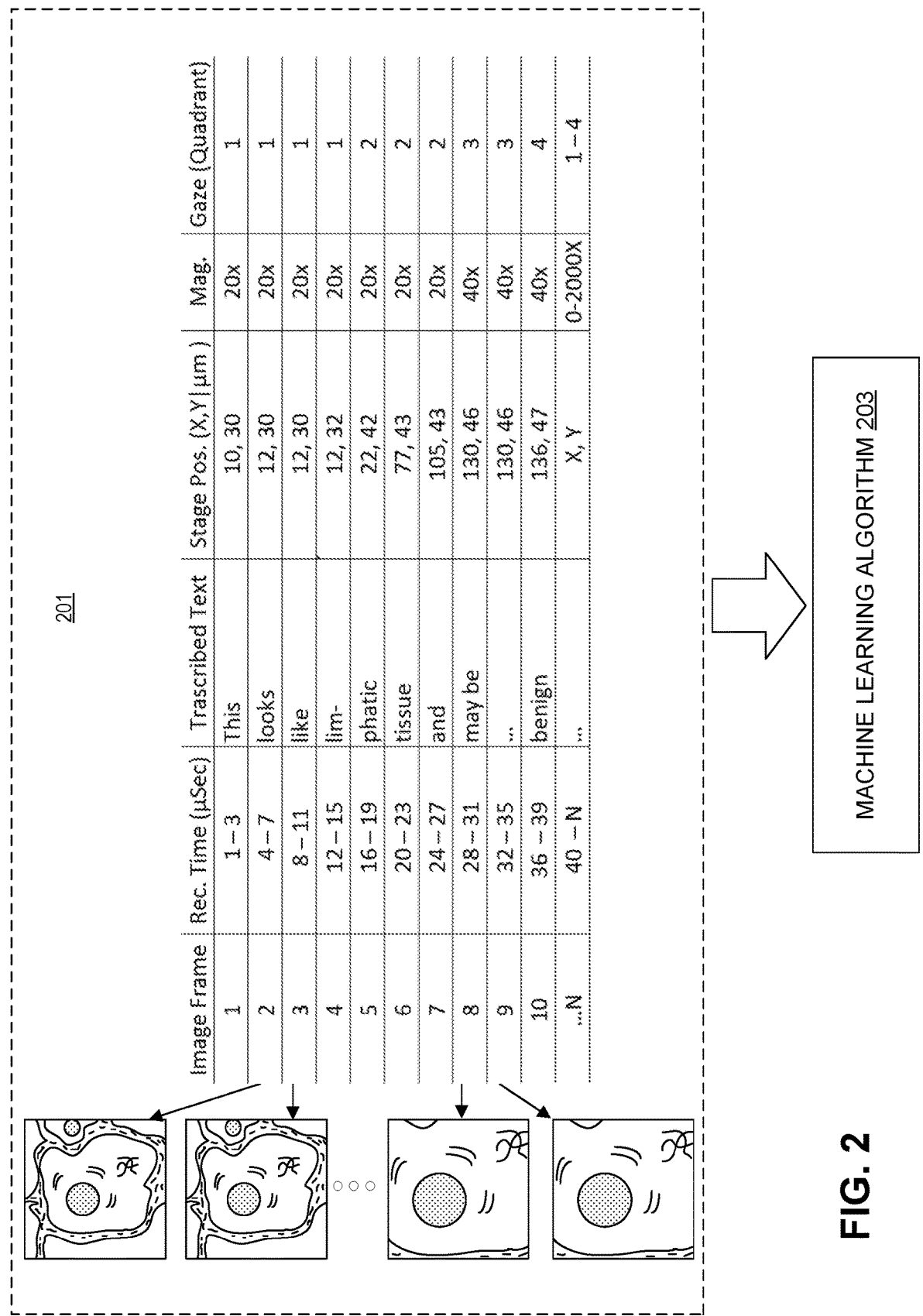
FIG. 2 illustrates a pathology database to train a machine learning algorithm, in accordance with an embodiment of the disclosure.

FIG. 2 illustrates a pathology database 201 to train a machine learning algorithm 203, in accordance with an embodiment of the disclosure. Pathology database 201 may be created using a system like system 100 of FIG. 1, and may be stored on storage 123. As shown in the depicted embodiment, pathology database 201 includes pathology images (e.g., video or still frames) that were captured by a digital camera (e.g., digital camera 103). The pathology images are indexed with respect to their frame number, recording time, the voice annotation of the pathologist (transcribed), microscope stage position, magnification they were collected at, and location of pathologist gaze. One skilled in the art will appreciate that system 100 depicted in FIG. 1 can be used to create a database with any number of dimensions and inputs and is not restricted to those dimensions/inputs depicted here.

As illustrated a digital camera (e.g., digital camera 103) optically coupled to a microscope (e.g., microscope 101) may start recording images of pathology samples as a digital video or still frames. Each frame of the video is indexed with respect to its capture time. For example in the depicted embodiment, frame one was captured during the first three microseconds of recording, frame two was captured in the fourth through seventh microseconds of recording, etc. A microphone (e.g., microphone 105) may also record the voice annotation of a user of the microscope. The vocal annotations may be converted into text and/or indexed to their respective recording time and video frame. In the depicted embodiment, while frame one was captured (during the first three microseconds of recording) the pathologist said the word "this"; in subsequent frames the pathologist stated "looks like lymphatic tissue and may be benign."

The system may also record the position of the microscope stage and index it with respect to the recording time and the magnified pathology images. In the depicted embodiment, the location of the stage is measured with X, Y coordinates from a (0,0) point which is the lower left hand position of the stage, and the stage movement is measured in microns. However, in other embodiments the stage axis may be oriented differently (e.g., the (0,0) point is located at the bottom right hand position of the stage), the units of measurement may be different (e.g., mm, cm, etc.), and the Z position of the stage may also be recorded. Furthermore, "stage position" should be broadly construed because it is used to identify specific locations on samples, which one skilled in the art will appreciate may be achieved in any number of ways. In one embodiment, stage position is determined optically with respect to the dimensions of the slide being imaged, and not with respect to the microscope hardware. As shown, the magnification that a specific frame was viewed with is also recorded with respect to recording time, transcribed text, stage position, and gaze quadrant.

The user's gaze may also be indexed with respect to the other dimensions/inputs illustrated and discussed. In the depicted embodiment, the gaze of the user/pathologist is measured in quadrants; meaning the image the user sees is subdivided into four sub-images, and the system records which sub-image the user was looking at during the recording time. This may be achieved with hardware/software installed in the microscope, or other external systems, as one skilled in the art will appreciate that there are many different ways to detect gaze. Moreover, while the embodiment depicted here only illustrates very generally where the pathologist/microscope user was looking, in other embodiments the exact coordinates that the user was looking at are recorded.

In one embodiment, indexing the magnified pathology images and the voice annotation may include tagging the voice annotation of the user to a region of interest in the magnified pathology images. For instance, in the embodiment depicted above, the pathologist's diagnosis of "benign" is associated with stage position coordinates (136, 47) at 40× magnification, and he/she was looking in quadrants 3 and 4. This allows the machine learning algorithm 203 to know exactly where the pathologist was looking when the determination of "benign" was made. Further the machine learning algorithm 203 knows the history of examination (how much of the slide had been examined up to that point). In the depicted embodiment, the processing apparatus may further include logic that when executed by the processing apparatus causes the processing apparatus to convert the pathologist's voice annotation to text, and the text is indexed with respect to recording time and the magnified pathology images, among the other dimensions/inputs mentioned and discussed. In another or the same embodiment, the pathologist may be able to review the pathology images collected and directly annotate the image to show a region of interest (e.g., circle the cancer cells on the digital image, place a star next to an unknown cell formation, etc.) to make teaching machine learning algorithm 203 easier.

It is worth noting that more than one pathologist may look at and annotate a pathology sample. Additional database rows and/or columns may be added so that information from both pathologists is captured. Both of the pathologists' input can then be compared to generate a ground truth/argument regarding what is known about the sample/slide. Redundancy of information about a pathology sample may make the diagnosis in pathology database 201 more robust, and provide a larger sample size to train machine learning algorithm 203.

All of the inputs discussed above may be fed into machine learning algorithm 203 to train machine learning algorithm 203 to recognize regions of interest in pathology samples. Machine learning algorithm 203 may be based on a neural-network type approach or other methods such as association rule learning, deep learning, inductive logic programming, decision tree learning, support vector machines, Bayesian networks, reinforcement learning, clustering, representation learning, similarity and metric learning, sparse dictionary learning, genetic algorithms, or the like. Additionally, machine learning algorithm 203 may include a number of different algorithms running in parallel or at discrete intervals.

Figure 3:
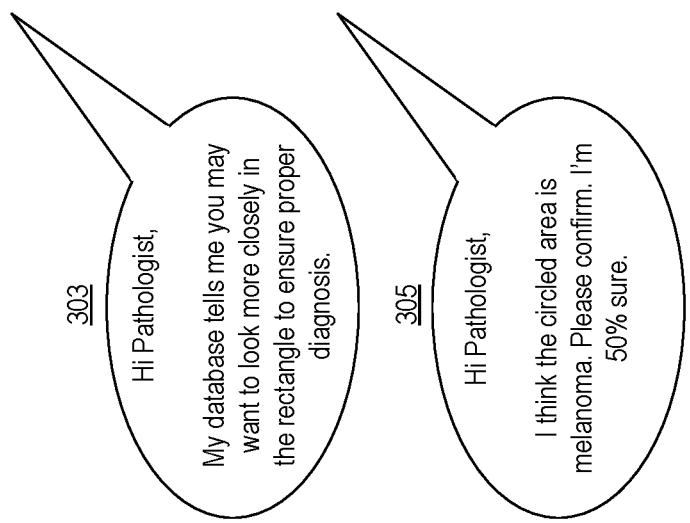
FIG. 3 illustrates what a pathologist might experience using the system of FIG. 1, in accordance with an embodiment of the disclosure.
Figure 3:
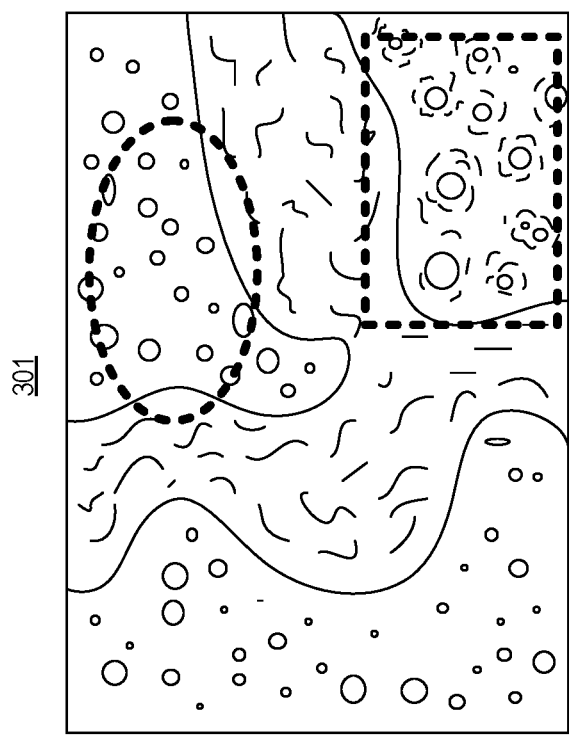

FIG. 3 illustrates what a pathologist might experience using system 100 of FIG. 1, in accordance with an embodiment of the disclosure. Image 301 is what a user/pathologist might see when looking through microscope 101. In one embodiment image 301 is projected onto screen 107. After inspecting the pathology sample for a few minutes, a speaker (e.g., speaker 125 of FIG. 1) may output several statements like statement 303 (letting the user/pathologist know they passed over a spot on the slide that has a potential region of interest) and statement 305 (telling the user a diagnosis of a structure in the one or more regions of interest, and outputting a confidence interval for the diagnosis). As shown the regions of interest and potential regions of interest may be highlighted (e.g., outlined) in image 301. The outline may appear on a screen or in the eyepiece of the microscope. In one embodiment, highlighting may include laser light shining directly on the sample, or any other way to alert the pathologist examining the sample.

In addition to receiving guidance from the machine learning algorithm, a pathologist may be able to start a video chat application either by interacting with the GUI or by calling for help ("Ok microscope, call a breast pathologist"). The video feed from the microscope may then be sent to a remote proctor to view. The remote proctor may be able to communicate directly with the local pathologist and system 100.

More proctors/specialists can be added as needed. This proctoring capability can also be used for student evaluation.

The proctoring capability may be combined with the machine learning algorithm: if the system detects a rare diagnosis, it could suggest calling an expert or even automatically do it. This capability could also be expanded to enable consensus pathology, where each slide is always reviewed by a number of pathologists simultaneously and a diagnosis is made only when a consensus has been achieved (e.g., initially three pathologists are connected, if they disagree a fourth pathologist is added etc. until the desired level of agreement is reached).

Figure 4:
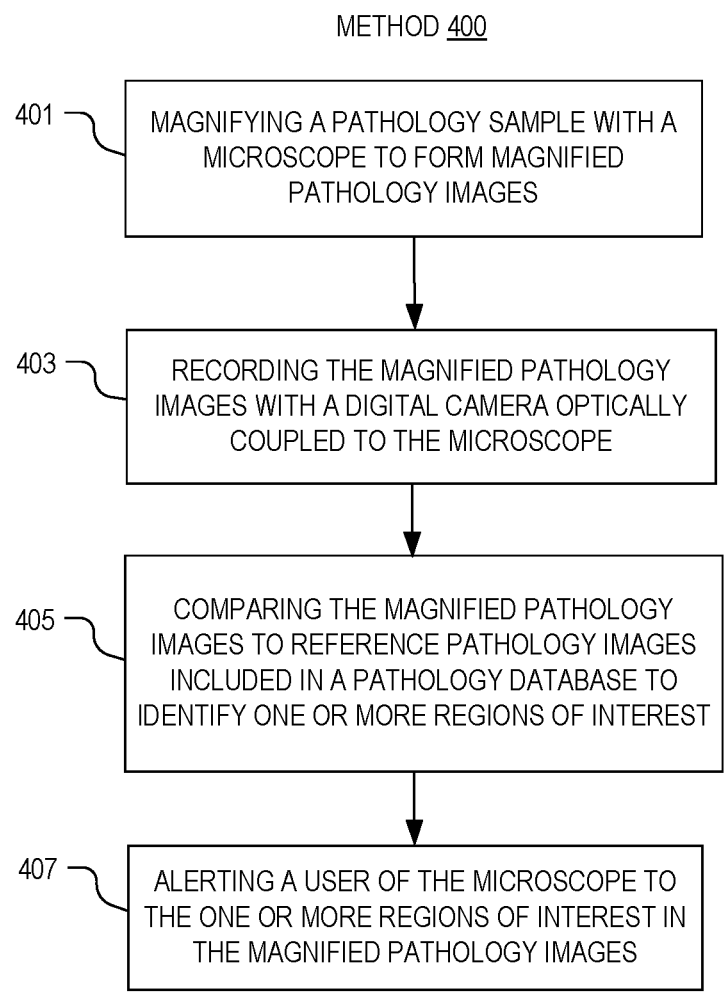
FIG. 4 is a flow chart illustrating a method of pathology diagnosis, in accordance with several embodiments of the disclosure.

FIG. 4 is a flow chart illustrating a method 400 of pathology diagnosis, in accordance with several embodiments of the disclosure. The order in which some or all of process blocks 401-407 appear in method 400 should not be deemed limiting. Rather, one of ordinary skill in the art having the benefit of the present disclosure will understand that some of method 400 may be executed in a variety of orders not illustrated, or even in parallel.

Block 401 illustrates magnifying a pathology sample with a microscope to form magnified pathology images. This may be done manually, by adjusting nobs on a microscope, or may be performed digitally using a computer system to control the microscope. In one embodiment, the microscope could also automatically zoom/move the slide so that the most relevant part of the slide (in order to make the diagnosis) is shown to the pathologist first. This feature could be combined with a slide feeding apparatus to greatly speed up pathologist workflow.

Block 403 shows recording the magnified pathology images with a digital camera optically coupled to the microscope. A processing apparatus may receive magnified pathology images from the digital camera either wirelessly or by wired transmission.

Block 405 describes comparing the magnified pathology images to reference pathology images included in a pathology database to identify one or more regions of interest in the magnified pathology images. In one embodiment, the one or more regions of interest include at least one of diseased portions of the pathology sample, or atypical cells in the pathology sample. The processing apparatus may run a machine learning algorithm to identify the one or more regions of interest, and the machine learning algorithm may be trained to identify regions of interest using the pathology database (see supra FIG. 2). As stated above, the pathology database may include annotations from a pathologist corresponding to the reference pathology images in the pathology database. The machine learning algorithm may use the annotations from the pathologist in conjunction with the reference pathology images to identify one or more regions of interest in the magnified pathology images.

In one embodiment, the pathology database further includes magnification information, and location information to identify a position on the reference pathology images. The machine learning algorithm may be trained by, and use the location information and the magnification information about, the reference pathology images to identify the one or more regions of interest in the magnified pathology images. In one embodiment, the pathology database further includes a plurality of reference pathology images of the same disease to train the machine learning algorithm (e.g., the database may have many images of melanoma).

Block 407 shows alerting a user of the microscope to the one or more regions of interest in the magnified pathology images. This may involve the processing apparatus outputting instructions to a microphone to output speech, highlight a portion of a screen, or moving (e.g., vibrate) a piece of equipment. In one embodiment, the machine learning algorithm outputs a diagnosis of a structure in the one or more regions of interest. In another or the same embodiment, the machine learning algorithm may output a confidence interval for the diagnosis, based on the reference pathology images in the pathology database.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system, comprising:
   a microscope configured to magnify a pathology sample;
   a camera positioned to record magnified pathology images from the microscope;
   a display configured to show the magnified pathology images; and
   a processing apparatus coupled to the camera and the display, wherein the processing apparatus includes a machine learning algorithm disposed in logic, and wherein the processing apparatus includes instructions that when executed by the processing apparatus cause the system to perform operations, including:
      identifying, using the machine learning algorithm, one or more regions of interest in the magnified pathology images and outputting a corresponding diagnosis associated with a structure in the one or more regions of interest;
      determining the one or more regions of interest identified by the machine learning algorithm are deemed to be insufficiently reviewed by a user of the system by tracking if the one or more regions of interest were in the user's field of view for less than a threshold amount of time, and wherein the one or more regions of interest that are deemed to be insufficiently reviewed are further determined by employing at least one of location on the pathology sample or level of magnification of the microscope; and alerting the user that the one or more regions of interest are deemed to be insufficiently reviewed when the corresponding diagnosis indicates the one or more regions of interest include at least one of diseased portions of the pathology sample or atypical cells in the pathology sample.

2. The system of claim 1, further comprising a network connection coupled to the processing apparatus, wherein the processing apparatus includes additional instructions that when executed by the processing apparatus cause the system to perform further operations, including:

receiving instructions from the user of the system to initiate a video chat with a third party via the network connection;

starting the video chat on the display; and sharing one or more images included in the plurality of magnified pathology images with the third party via the network connection.

3. The system of claim 1, wherein the processing apparatus, using the machine learning algorithm, is configured to identify the one or more regions of interest in real time, and wherein the machine learning algorithm is trained to identify the one or more regions of interest using reference pathology images in a pathology database coupled to the processing apparatus.

4. The system of claim 3, wherein the pathology database includes annotations corresponding to the reference pathology images in the pathology database, and wherein the machine learning algorithm is trained using both the annotations and the reference pathology images to identify the one or more regions of interest in the magnified pathology images.

5. The system of claim 3, wherein the machine learning algorithm includes a neural network.

6. The system of claim 5, wherein the machine learning algorithm includes a plurality of algorithms running in parallel or intervals, and wherein at least one of the plurality of algorithms includes the neural network.

7. A method, comprising:

receiving, with a processing apparatus, magnified pathology images of a pathology sample from a camera;

identifying, using the processing apparatus, one or more regions of interest in the magnified pathology images, wherein the processing apparatus includes a machine learning algorithm disposed in logic to identify the one or more regions of interest and output a corresponding diagnosis associated with a structure in the one or more regions of interest;

determining the one or more regions of interest identified by the machine learning algorithm are deemed to be insufficiently reviewed by a user of the processing apparatus by tracking if the one or more regions of interest were in the user's field of view for less than a threshold amount of time, and wherein the one or more regions of interest that are deemed to be insufficiently reviewed are further determined by employing at least one of location on the pathology sample or level of magnification of the magnified pathology images; and alerting the user that the one or more regions of interest are deemed to be insufficiently reviewed when the corresponding diagnosis indicates the one or more regions of interest include at least one of diseased portions of the pathology sample or atypical cells in the pathology sample.

8. The method of claim 7, further comprising informing the user of the corresponding diagnosis with at least one of a display or a speaker coupled to the processing apparatus.

9. The method of claim 8, further comprising:

receiving instructions from the user to initiate a video chat with a third party via a network connection coupled to the processing apparatus; and starting the video chat on the display.

10. The method of claim 9, wherein starting the video chat includes sharing one or more images in the magnified pathology images with the third party via the network connection.

11. The method of claim 7, wherein the machine learning algorithm is trained to identify the one or more regions of interest using reference pathology images disposed in a pathology database coupled to the processing apparatus.

12. The method of claim 7, wherein the machine learning algorithm includes a neural network.

13. The method of claim 12, wherein the machine learning algorithm includes a plurality of algorithms running in parallel or intervals, and wherein at least one of the algorithms includes the neural network.

14. A non-transitory computer-readable storage medium having stored thereon instructions which, when executed by a processing apparatus, cause the processing apparatus to perform operations comprising:

receiving, with the processing apparatus, magnified pathology images from a camera optically coupled to a microscope;

identifying, using the processing apparatus, one or more regions of interest in the magnified pathology images, wherein the non-transitory computer-readable storage medium includes a machine learning algorithm configured to identify the one or more regions of interest and outputting a corresponding diagnosis associated with a structure in the one or more regions of interest;

determining the one or more regions of interest identified by the machine learning algorithm are deemed to be insufficiently reviewed by a user of the processing apparatus by tracking if the one or more regions of interest were in the user's field of view for less than a threshold amount of time, and wherein the one or more regions of interest that are deemed to be insufficiently reviewed are further determined by employing at least one of location on the pathology sample or level of magnification of the microscope; and alerting the user that the one or more regions of interest are deemed to be insufficiently reviewed when the corresponding diagnosis indicates the one or more regions of interest include at least one of diseased portions of the pathology sample or atypical cells in the pathology sample.

15. The non-transitory computer-readable medium of claim 14, wherein the instructions, which when executed by the processing apparatus, cause the processing apparatus to perform further operations comprising:

informing a user, via at least one of a display or a speaker coupled to the processing apparatus, of the corresponding diagnosis.

16. The non-transitory computer-readable medium of claim 15, wherein the instructions, which when executed by the processing apparatus, cause the processing apparatus to perform further operations comprising:

receiving instructions from the user to initiate a video chat with a third party via a network connection coupled to the processing apparatus; and starting the video chat on the display.

17. The non-transitory computer-readable medium of claim 16, wherein starting the video chat includes sharing one or more images in the plurality of magnified pathology images with the third party via the network connection.

18. The non-transitory computer-readable medium of claim 14, wherein the machine learning algorithm is trained to identify the one or more regions of interest using reference pathology images disposed in a pathology database coupled to the processing apparatus.

19. The non-transitory computer-readable medium of claim 14, wherein the machine learning algorithm includes a neural network.

20. The system of claim 1, wherein when the corresponding diagnosis associated with the structure in the one or more regions of interest is benign, alerting to the user of a benign diagnosis for the one or more regions of interest.

* * * * *